(12) United States Patent
Levon et al.

(10) Patent No.: US 6,827,840 B2
(45) Date of Patent: Dec. 7, 2004

(54) CHIRAL LIGAND EXCHANGE POTENTIOMETRY AND ENANTIOSELECTIVE SENSORS

(75) Inventors: Kalle Levon, New York, NY (US); Bin Yu, Brooklyn, NY (US); Yanxiu Zhou, Brooklyn, NY (US)

(73) Assignee: Polytechnic University, Brooklyn, NY (US)

( * ) Notice: Subject to any disclaimer, the term of this patent is extended or adjusted under 35 U.S.C. 154(b) by 0 days.

(21) Appl. No.: 10/170,903

(22) Filed: Jun. 13, 2002

(65) Prior Publication Data

US 2003/0230496 A1 Dec. 18, 2003

(51) Int. Cl.[7] .......................................... G01N 27/327
(52) U.S. Cl. ................................ 205/787; 205/775
(58) Field of Search ............................ 205/775, 787, 205/789, 777.5; 204/403.01, 415, 416, 418

(56) References Cited

U.S. PATENT DOCUMENTS 6,033,630 A * 3/2000 Hinton et al. .................. 422/98

OTHER PUBLICATIONS

Kataky et al. ("Functionalized alpha–Cyclodextrins as Potentiometric Chiral Sensors," Analyst, Aug. 1992, vol. 117), pp. 1113–1117.*

Ng et al. ("Chiral discrimination of enantiomers with a self–assembled monolayer of functionalized beta–cyclodextrins on Au surfaces," Tetrahedron Letters 43 (2002) 2863–2866).*

Troughton et al. ("Monolayer Films Prepared by the Spontaneous Self–Assmbly of Symmetrical and Unsymmetrical Dialkyl Sulfides from Solution onto Gold Substrates: Structure, properties, and Reactivity of Constituent Functional Groups," Langmuir 1988, 4, 365–385).*

* cited by examiner

Primary Examiner—Alex Noguerola
(74) Attorney, Agent, or Firm—John C. Pokotylo; Straub & Pokotylo

(57) ABSTRACT

Enantiomeric resolution is realized by combining an electrochemical method with ligand exchange (LE) in a novel electrochemical method named chiral ligand exchange potentiometry. Chiral selector ligands preferentially recognize certain enantiomers and undergo ligand exchange with the enantiomeric labile coordination complexes to form diastereoisomeric complexes. These complexes can form in solution and be recognized by an unmodified electrode, or they can be immobilized on the surface of a modified electrode (chiral sensor) incorporated with the chiral selector ligand by polysiloxane monolayer immobilization (PMI). Considerable stereoselectivity occurs in the formation of these diastereoisomeric complexes, and their net charges (Nernst factors) are different, thus enabling enantiomers to be distinguished by potentiometric electrodes without any pre-separation processes.

21 Claims, 9 Drawing Sheets

(D-Asp)Cu(II)(N-CBZ-L-Asp)

(a)

(L-Asp)Cu(II)(N-CBZ-L-Asp)

(b)

(D-Asp)Cu(II)(N-CBZ-L-Asp)

(a)

(L-Asp)Cu(II)(N-CBZ-L-Asp)

(b)

CHIRAL LIGAND EXCHANGE POTENTIOMETRY AND ENANTIOSELECTIVE SENSORS

§1. BACKGROUND

§1.1 Field of the Invention

The present invention concerns detecting an enantiomer or enantiomers in general, and detecting or and distinguishing enantiomeric compounds by chiral ligand exchange potentiometry (CLEP) in particular.

§1.2 Related Art

Distinguishing enantiomers, such as amino acids has important applications to analytical chemistry, biotechnology, and medical sciences. For example, a simple monitoring system for distinguishing enantiomers would be extremely useful in biotechnological processes and medical diagnosis. The importance of chiral drugs that express different biological activities, and therefore often different therapeutic properties, for different enantiomers has been recognized by both pharmacologists and regulatory authorities.

Known techniques for detecting enantiomers include high-performance liquid chromatography ("HPLC"), capillary zone electrophoresis ("CZE"), and chiral ligand-exchange chromatography ("CLEC"). CLEC, which has been the most widely used of these techniques, accomplishes enantiomer separation by forming transient ternary copper complexes with an optically active amino acid derivative. See, e.g., the article V. A. Davankov, et al., *Ligand Exchange Chromatography*, 47 (1988) (hereafter referred to as "the Davankov article I"). With CLEC, an optically active bidentate ligand that functions as the chiral selector is grafted onto the support surface of the stationary phase. Ternary complexes are formed with amino acid analytes loaded with Cu(II) ions, which are a component of the mobile phase. See, e.g., the articles: S. Ahuja, J. *Amer. Chem. Soc.*, (1996); and the Davankov article I. (These articles are incorporated herein by reference.) Separation occurs if the free energies of formation for the diastereoisomeric complexes are sufficiently different.

Unfortunately, the CLEC, HPLC and CZE techniques for enantiomeric resolution of compounds do not have a detection system that can distinguish different enantiomers. Instead, the enantiomers must be separated before detection.

A known technique for distinguishing enantiomers is the electrochemical enzyme biosensor method. Electrochemical enzyme biosensors are amperometric detection systems that couple the enantioselectivity of the enzyme and the sensitivity of the amperometry. Unfortunately, however, the biological components in these biosensors limit their effectiveness. In particular, problems arise concerning long-time stability, irreversible deactivation at high temperatures or under harsh chemical environments, and operation in organic phases. See, e.g., the article F. Scheller, et al., *Biosensors*, (1992).

The drawbacks of techniques such as HPLC, CZE, CLEC, and the electrochemical enzyme biosensor method limit their potential applications. For example, HPLC, CZE, and CLEC do not have detection systems that can distinguish enantiomers. The electrochemical enzyme biosensor's biological components limit its use. A method with a detection system that can distinguish enantiomers and that is not limited by biological components would overcome these drawbacks.

In view of the shortcomings of previous techniques, a better way to detect and distinguish enantiomers is needed.

§2. SUMMARY OF THE INVENTION

The present invention provides novel electrochemical methods for distinguishing or detecting enantiomers.

The present invention provides a novel electrochemical enantiodiscrimination method, referred to as "chiral ligand exchange potentiometry" (CLEP), which combines an electrochemical technique with ligand exchange. In a first embodiment, chiral ligand exchange potentiometry (CLEP) involves an electrode in contact with a solution of chiral selector ligands and enantiomers complexed with metal ions (labile coordination complexes). Ligand exchange occurs between the labile coordination complexes and the chiral selector ligands to form complexes of metal ions, chiral selector ligands, and enantiomers which are diastereoisomeric complexes. Diastereoisomeric complexes with different enantiomers have different net charges (Nernst factors). It is this difference in net charges that allows the potentiometric electrode to distinguish them.

In another embodiment, the present invention achieves enantiomer identification using a modified electrode (chiral sensor). Chiral selector ligands are incorporated into the modified electrode, thereby enabling the electrode to act as molecular sensors that recognize one enantiomer and preferentially immobilize that type of enantiomer on the surface of the electrode. In this embodiment, the solution needn't include the chiral selector ligand. Again, the net charge of the diastereoisomeric complex formed between the chiral selector ligand on the modified electrode and the enantiomer identifies the enantiomer.

§3. BRIEF DESCRIPTION OF DRAWINGS

§4. DETAILED DESCRIPTION

Figure 1:
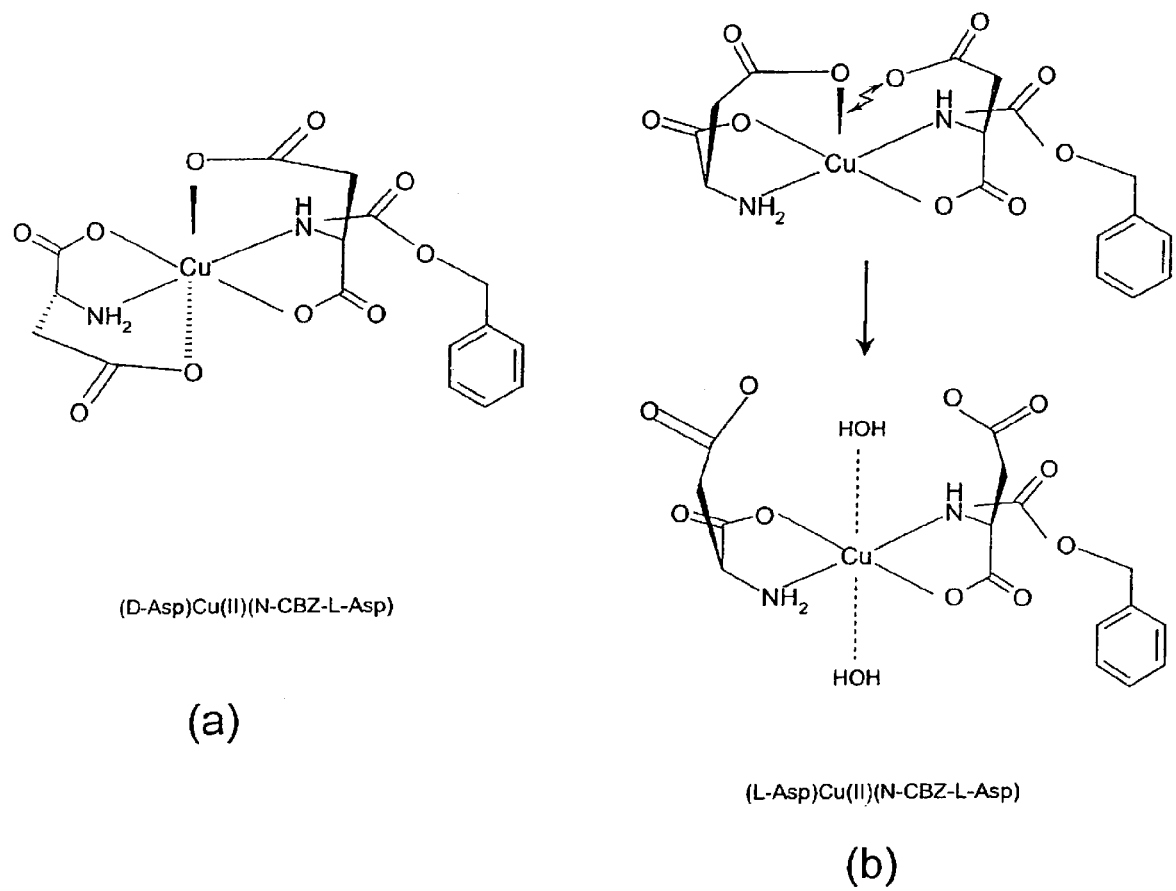
FIG. 1 depicts a first scheme having the structure of (a) the more stable complex (D-Asp)Cu(II)(N-CBZ-L-Asp), [DCuL], and (b) the less stable complex (L-Asp)Cu(II)(N-CBZ-L-Asp), [LCuL].

The present invention involves novel methods for detecting and/or distinguishing enantiomers by electrochemical techniques involving a combination of potentiometry and chiral ligand exchange. The following description is presented to enable one skilled in the art to make and use the invention, and is provided in the context of particular embodiments and methods. Various modifications to the disclosed embodiments and methods will be apparent to those skilled in the art, and the general principles set forth below may be applied to other embodiments, methods, and applications. Thus, the present invention is not intended to be limited to the embodiments and methods shown and the inventors regard their invention as the following disclosed methods, apparatus, and materials and any other patentable subject matter to the extent that they are patentable.

The present invention involves a technique termed "chiral ligand exchange potentiometry". Given a solution containing enantiomers, metal ions, and chiral ligands, a (unmodified) potentiometric electrode can distinguish enantiomers by the different Nernst factors (or net charges) of the complexes they form. The electrode may be a semiconducting electrode, and it may be modified (to incorporate the chiral ligands on the surface of the electrode) or unmodified. The electrode measures the potential of complexes formed between an enantiomer, metal ion, and chiral ligand. Enantiomers are distinguished based on the potential(s) of their complexes, which is measured by the potentiometric electrode.

In the following, functions that may be performed by the present invention are introduced in §4.1. Then, the theory behind the present invention is described in §4.2. Thereafter, an exemplary embodiment of the present invention is described in §4.3. Then, potentiometric electrodes are described in §4.4. In §4.5, specific embodiments of potentiometric electrodes, including the chiral sensor, are described.

§4.1 Functions

The present invention may function to detect and/or distinguish enantiomers. Also, the present invention may function to fabricate a potentiometric sensor for such a purpose.

§4.2 Theory of Chiral Ligand Exchange Potentiometry

Potentiometry recognizes specific analytes in solution by measuring the potential of a reaction of interest occurring in the solution. Although potentiometry is a common technique for quantitating ion concentrations (e.g., $H^+$ ions in pH measurement), it has not been employed as a device to resolve chiral species. The present invention describes methods for potentiometric discrimination of enantiomers by allowing a reaction of interest to occur for which different enantiomers form different complexes, those complexes yielding different potentials.

In the present invention, the reaction of interest may be a ligand exchange. The reaction solution of the present invention initially contains enantiomers, modified chiral molecules, and metal ions. Initially, the enantiomers complex with metal ions to form labile coordination complexes. Although the labile coordination complexes are formed first, neither complex is particularly stable because of steric hindrance. The modified chiral molecule, or chiral selector ligand, on the other hand, can form a more stable complex with the metal ion. Therefore, when the labile coordination complexes encounter the chiral selector ligands, ligand exchange occurs and new diastereoisomeric adducts form consisting essentially of a chiral selector ligand, a metal ion, and an enantiomer. The difference in free energy of formation determines the rate of formation of each diastereoisomeric complex. The free energy of formation of each complex, in turn, is determined by its formation constants as well as its concentration. The diastereoisomeric complexes formed for each of the two enantiomers have different net charges (Nernst factors), thus enabling the two enantiomers to be distinguished by potentiometry.

The mechanism of distinguishing enantiomers is based on the thermodynamic and kinetic factors governing the formation of each enantiomer's diastereoisomeric complex, and the spatial structure and net charge that results. In the present invention, stereochemical hindrance causes each enantiomer to bind the diastereoisomeric complex a certain way. Different net charges result from such stereochemical distinctions in the complexes. Since potentiometry is an electrochemical technique that measures an equilibrium potential, i.e., the potential at zero current, of the sensor vs. a suitable reference electrode, it can distinguish between the diastereoisomeric complexes based on their net charges. Additionally, the predominant form of both the enantiomer and the chiral selector ligand may exist as zwitterions, or neutral amino acids, at a certain pH, or within a certain pH range. At this pH (range), the electrode's response is substantially or solely due to the charges of the diastereoisomeric complexes in solution. However, CLEP is not limited to a pH range at which enantiomers are neutral. The enantiomers can be distinguished provided the net charge of the two diastereoisomeric complexes is different and results in a measurable potential. The potential response, therefore, not only arises from the charge of the enantiomers themselves, but also from the net overall charge of the diastereoisomeric complexes.

Initially, only labile coordination complexes and chiral selector ligands are present in the reaction solution, and the potential difference between enantiomeric labile coordination complexes is not great enough for them to be distinguished by the electrode. Although both complexes have different stabilities and conformations, these differences are too small to be detected by electrochemical discrimination or by normal spectroscopic techniques. See, e.g., the article V. A. Davankov, et al., *J. Chem. Soc. Dalton Transition*, 1012–1016 (1972), hereafter referred to as "the Danakov article II". (This article is incorporated herein by reference.)

In the present invention, the enantiomers may be amino acids, chiral drugs and other enantiomers. Those enantiomers used in this technique typically should be tridentate compounds, such as amino acids (e.g., histidine, glutamic acid, and aspartic acid), amino acid derivatives (e.g., N-2, 4-DNP-glutamic acid, N-2,4-DNP-DL-citrulline, N-carbobenzoxy-L- or D-aspartic acid (N-CBZ-Asp)), and chiral drugs (e.g., kynurenine, folinic acid, etc.) that can displace a water molecule from the axial position of the complex. The chiral selectors should be tridentate compounds and have a bulky substituent, such as N-CBZ-L- or D-Asp for chiral aspartic acid, N-CBZ-L- or D-glumatic acid for glumatic acid, N-(2-naphthalenesulfonyl-L- or D-histidine) for chiral histidine, etc. The metal ion could be Cu(II), Cd(II), Al(III), Ni(II), Pb(II), Zn(II) ions, etc. Carboxyl groups of tridentate amino acids can displace the water molecule from the axial position of the complex, thereby enabling a new diastereoisomeric adduct to be formed. Such compounds are adsorbed preferentially onto the axial position of the complex, displacing the water molecule and thus providing different net charges for diastereoisomeric complexes. Other important characteristics of the chiral selector ligand and the amino acid of interest are their size and shape. For the diastereoisomeric complex to be stable, the size and shape of the three tridentate groups' lengths should be comparable. A complex of non-matched amino acid and chiral selector ligand can be formed, but is more labile than a matched complex.

§4.3 Exemplary Embodiment

In an exemplary embodiment of the present invention, metal ion copper(II) and enantiomers L- and D-aspartate (L-Asp and D-Asp) are present in the solution as labile coordination complexes, [Cu(D-Asp)$_2$] and [Cu(L-Asp)$_2$]. As mentioned previously, the potential difference between enantiomeric labile coordination complexes is not great enough for them to be distinguished by the electrode, nor are they particularly stable. A chiral selector ligand, N-carbobenzoxy-L-aspartic acid (N-CBZ-L-Asp), undergoes ligand exchange with the labile coordination complexes to form more stable diastereoisomeric complexes (D-Asp)Cu(N-CBZ-L-Asp) and (L-Asp)Cu(N-CBZ-L-Asp). However, (D-Asp)Cu(N-CBZ-L-Asp) is energetically preferred.

Potentiometric sensors work through the measurement of an equilibrium potential, i.e., the potential at zero current, of the sensor relative to a suitable reference electrode. These potentials are a function of the activity of the species in solution, not of their concentration. The concentration of chiral selector, metal ions, and pH of medium can be optimized, and it is desirable to control such parameters to obtain the maximum difference between enantiomers. (See, e.g., FIGS. 5 and 6.)

Some embodiments of the detection system of the present invention are sensitive to pH. In the case of aspartic acid as the analyte, for example, the pH of the solution influences the detection system greatly because of aspartic acid's three acid/base equilibria. In the exemplary embodiment of the present invention, maximum potential difference is observed at pH 2.3, as indicated by the pH dependence of output of the ITO electrode for $1 \times 10^{-5}$ (○), $2 \times 10^{-5}$ (□), and $1.2 \times 10^{-4}$ (Δ) M aspartic acid (see FIG. 5). The pH of the reaction solution is therefore adjusted to this value by a 0.1 M KCl-phthalate buffer.

Two competitive pathways exist in the formation of diastereoisomeric complexes since cupric ion can complex with either the D- or L-isomers (Cu(D- or L-Asp)$_2$) or the chiral selector ligand (Cu(N-CBZ-L-Asp)$_2$) before ligand exchange occurs and the preferred diastereoisomeric complex ((D-Asp)Cu(N-CBZ-L-Asp)) is formed. The mixing order, or sequence of adding ligands to form complexes, is therefore important in clarifying the discrimination mechanism of chiral ligand exchange potentiometry. In the exemplary embodiment of the present invention, three different mixing orders were tested and time dependence of complex formation was measured by potentiometry. The mixing orders allowed different combinations of components to be added to the solution in various orders:

Order I: cupric ions complexed with L- or D-Asp to form [Cu(L-Asp)$_2$] or [Cu(D-Asp)$_2$] were added to the solution first, and then the chiral selector ligand N-CBZ-L-Asp was added to the above solution to substitute for one of the Asp:

(1) [Cu(L- or D-Asp)$_2$]+(2) [N-CBZ-L-Asp] Order I

Order II: cupric ions complexed with the chiral selector ligand N-CBZ-L-Asp were added to the solution first to form [Cu(N-CBZ-L-Asp)$_2$] and then L- or D-Asp was added to the solution:

(1) [Cu(N-CBZ-L-Asp)$_2$]+(2) [L- or D-Asp] Order II

Order III: N-CBZ-L-Asp and D- and L-Asp were mixed together first and then Cu(II) was added:

[(N-CBZ-L-Asp)+(L- or D-Asp)]+(2) [Cu$^{2+}$] Order III

Figure 3:
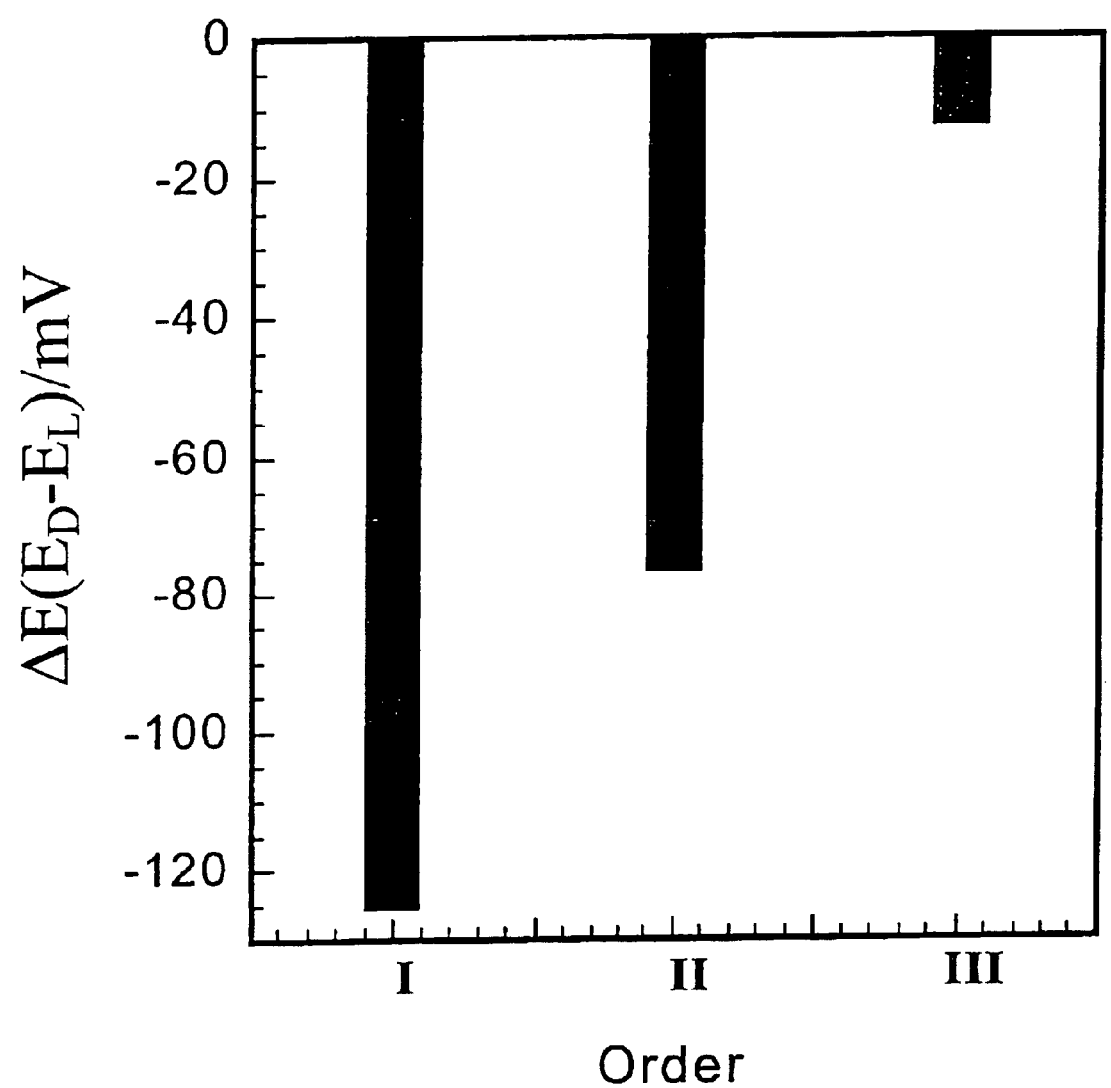
FIG. 3 is a graph that shows the influence of mixing order on complex formation.

Results indicated that, due to thermodynamic and kinetic factors, the best mixing order allowed L- or D-Asp to complex with Cu(II) first, before adding N-CBZ-L-Asp. FIG. 3 illustrates the influence of mixing order on enantioselectivity. It clearly demonstrates the existence of steric and electronic chiral recognition. The potential difference between D- and L-Asp in Order I is higher than that of Order II and Order III. The diastereoisomeric complexes had two chiral ligands coordinated to the cupric ions (shown in FIG. 1): the chiral selector ligand, N-CBZ-L-Asp, and an enantiomer analyte, D- or L-Asp. Asp was mixed with cupric ions first in Order I, allowing transient dibasic cupric complexes to form: [Cu(D- or L-Asp)$_2$]. As mentioned previously, labile coordination complexes [Cu(L-Asp)$_2$] and [Cu(D-Asp)$_2$] display identical physical properties and conformations, although such differences are not detectable by electrochemical or normal spectroscopic techniques. (See, e.g., the Davankov article II.) Both complexes were not particularly stable due to steric hindrance. Thus, diastereomeric adducts [(D-Asp)Cu(N-CBZ-L-Asp)] and [(L-Asp)Cu(N-CBZ-L-Asp)] formed when they encountered the chiral selector ligand, N-CBZ-L-Asp. Regarding Order II, the complex [Cu(N-CBZ-L-Asp)$_2$] was formed first. Thus, it was difficult for D- or L-Asp to approach the complex and further displace one N-CBZ-L-Asp from the tridentate, because of the bulky substitute group (-CBZ) on the N atom, which may produce serious steric hindrance. In Order III, there is a competitive process between the chiral selector ligand and D- or L-Asp. From a thermodynamic standpoint, Order II and Order III are the same.

Figure 4:
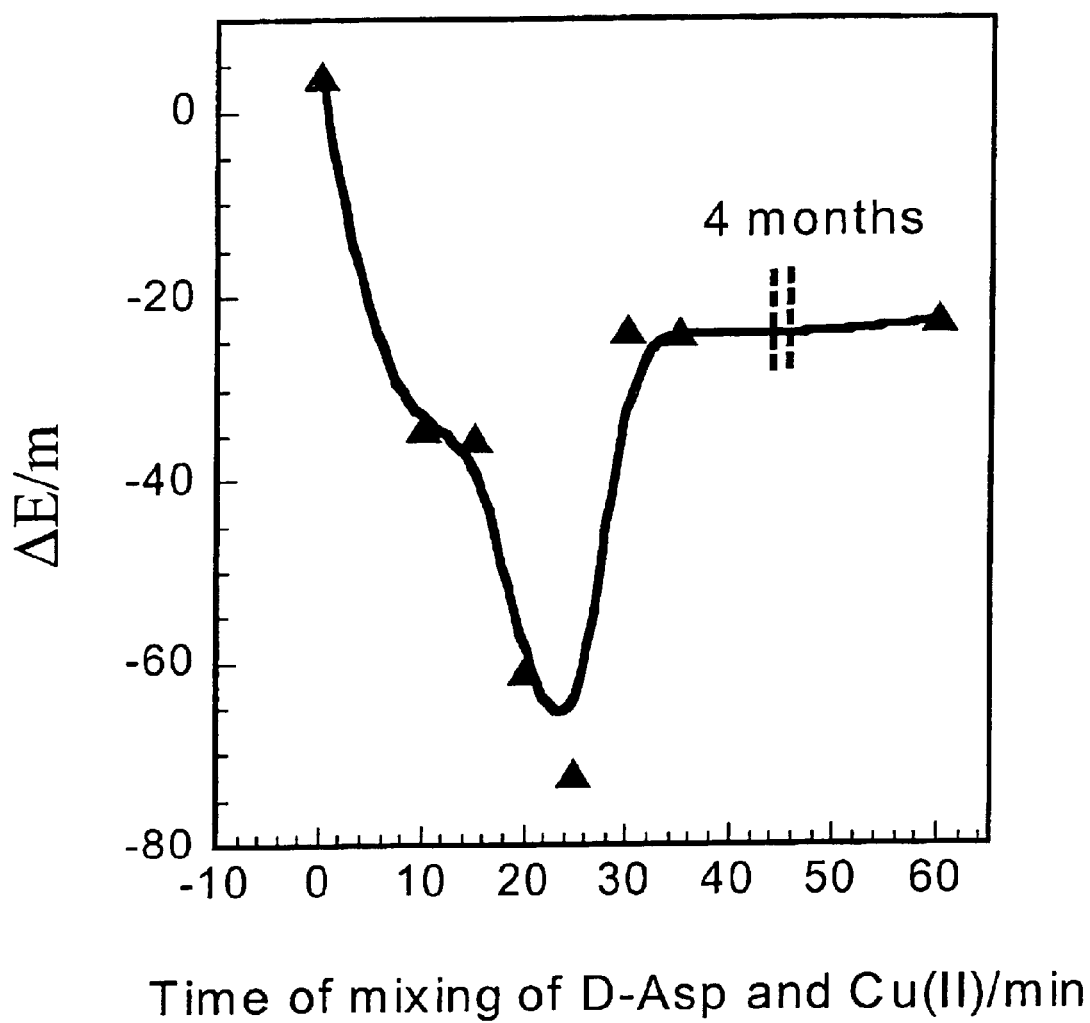
FIG. 4 is a graph that shows the influence of time on the mixing of D-Asp and Cu(II)/min.

The effect of mixing order in terms of the kinetics of formation should also be considered. For Order I, there are two processes for formation the complex: the process of forming [Cu(D- or L-Asp)$_2$] (process I), and the process of displacing D- or L-Asp from [Cu(D- or L-Asp)$_2$] by chiral selector ligand N-CBZ-L-Asp (process II). The influence of the time of mixing Cu(II) and D-Asp between 0 and 4 months was tested. The potential shifts to negative and reaches its maximum at 24 minutes, as shown in FIG. 4. First Cu(II) and D-Asp were mixed for 24 min and then N-CBZ-L-Asp was added immediately, after 30 minutes, and after 4 months. The potential responses were −23.9 when added immediately, −22.61 when added after 30 minutes and −23.65 mV when added after 4 months. Therefore, the rate-controlling step should be process I rather than process II.

Figure 6:
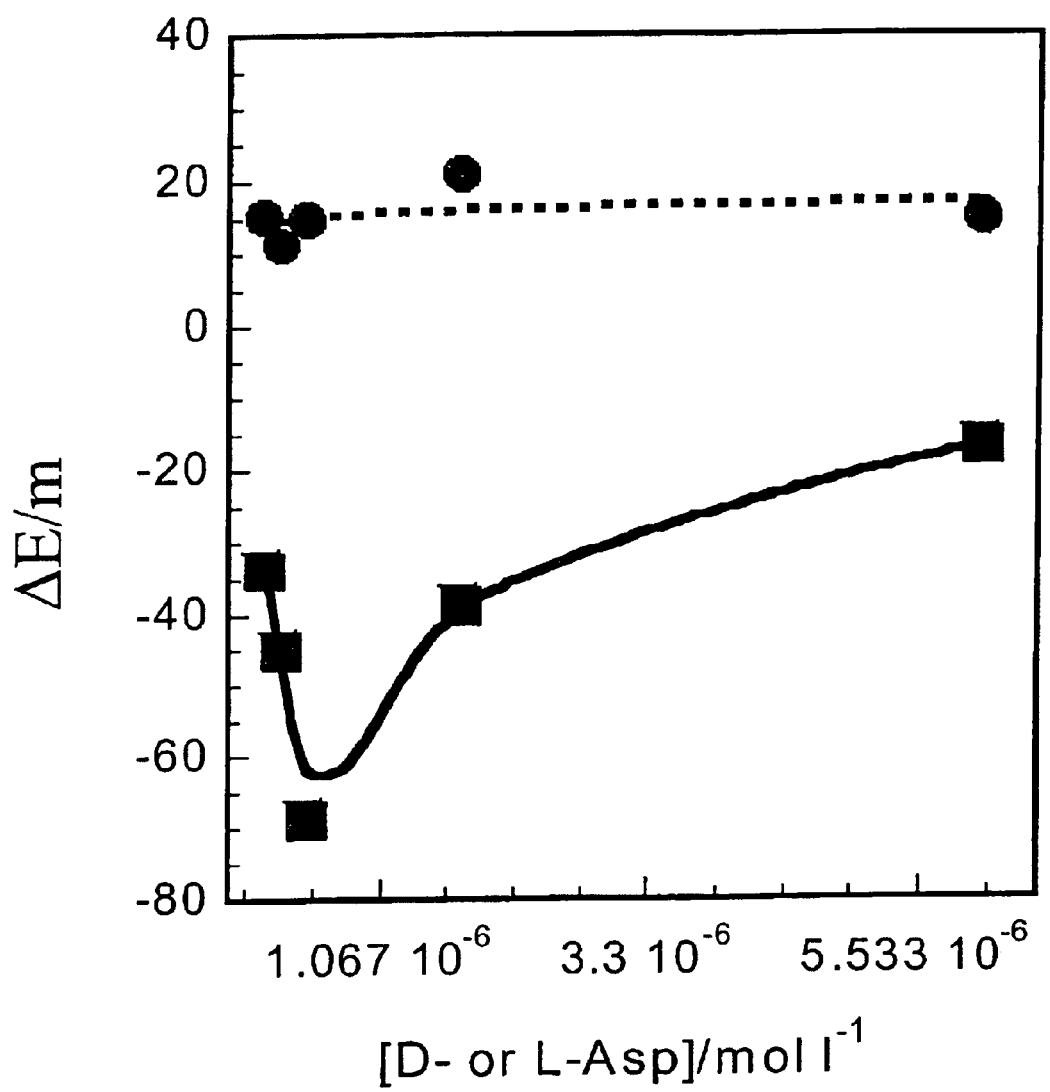
FIG. 6 is a graph that shows the effect of the concentration of N-CBZ-L-Asp on the measured potential.

Additionally, the concentration of the chiral selector ligand influences its recognition of the preferred enantiomer coordination complex. In the exemplary embodiment of the present invention, the influence of N-CBZ-L-Asp concentration on the recognition of D-Asp is shown in FIG. 6. When the concentration of D- or L-isomer of Asp and Cu(II) were $1.83 \times 10^{-6}$ mol/L and $2.5 \times 10^{-6}$ mol/L, respectively, the most efficient concentration of N-CBZ-L-Asp was about $5.0 \times 10^{-7}$ mol/L. The influence of the cupric ion concentration on the electrochemical recognition demonstrated that as the calibration range of Asp is from $10^{-8} \sim 10^{-5}$ mol/L, the optimal concentration of cupric ions was $2.5 \times 10^{-6}$ mol/L. The reaction solution should be adjusted accordingly.

Although both diastereoisomeric complexes contain a cupric ion and a chiral selector ligand, they have different amino acid isomers (L or D), which results in a different spatial conformation of the complex (see FIG. 1). The [(L-Asp)Cu(N-CBZ-L-Asp)] diastereoisomeric complex is more sterically hindered than the [(D-Asp)Cu(N-CBZ-L-Asp)] complex. The [(L-Asp)Cu(N-CBZ-L-Asp)] complex contains two carboxyl groups above the planar part of the molecule, resulting in a crowded space that hinders complexation. In fact, such a complex should be sterically prohibited. The meso [(D-Asp)Cu(N-CBZ-L-Asp)] complex is more energetically favorable, as shown by UV-vis spectral analysis (see FIG. 8). From FIG. 8, curve (□), the UV-Vis intensity of peaks (232 nm) of [(D-Asp)Cu(N-CBZ-L-Asp)] was increased due to the stronger complexion compared to [(Cu(N-CBZ-L-Asp)$_2$], and a new peak appeared at 278 nm. In the equally paired [(L-Asp)Cu(N-CBZ-L-Asp)] complex, both the carboxyl groups were in upper part of the planar (FIG. 1(b)). The crowded space would influence the complexion so that it is sterically prohibited. The intensity of peaks (232 nm) of meso D-Cu-L (FIG. 8 curve (□)) complex decreased compared to [(D-Asp)Cu(II)(N-CBZ-L-Asp)] and [Cu(II)(N-CBZ-L-Asp)$_2$] (FIG. 8 curve (○,Δ)).

The stereochemistry of the enantiomers' diastereoisomeric complexes results in different net charges (Nernst factors) for the complexes. According to the three-point interaction model of ligand exchange chromatography, at least three contacts should exist between the two ligands (enantiomer and chiral selector ligand) within the mixed-ligand structure (diastereoisomeric complex) to bring about the desired chiral recognition. As is common in LEC, these are the copper-mediated interactions between the electron-donating nitrogen and oxygen atoms of the chiral selector ligand N-CBZ-L-Asp and enantiomer Asp. The chiral selector ligand, N-CBZ-L-Asp, and the amino acid, D- or L-Asp, are held in place by two coordinate-covalent bonds. In the case of [(D-Asp)Cu(N-CBZ-L-Asp)], four carboxyl groups from two amino acids provided four electrons to the cupric ion. The −4 charge of these electrons coupled with the +2 charge of the cupric ion results in a net charge, or Nernst factor, of −2. In the case of [(L-Asp)Cu(N-CBZ-L-Asp)], on the other hand, not all of the amino acids' carboxyl groups could effectively axially complex with the cupric ion because of the complex's spatial structure. As a result, only two α-carboxyl groups' electrons contributed to the total net charge. These α-carboxyl groups provide two electrons, a −2 charge, coupled with the +2 charge of the cupric ion to yield a net charge of zero.

Figure 5:
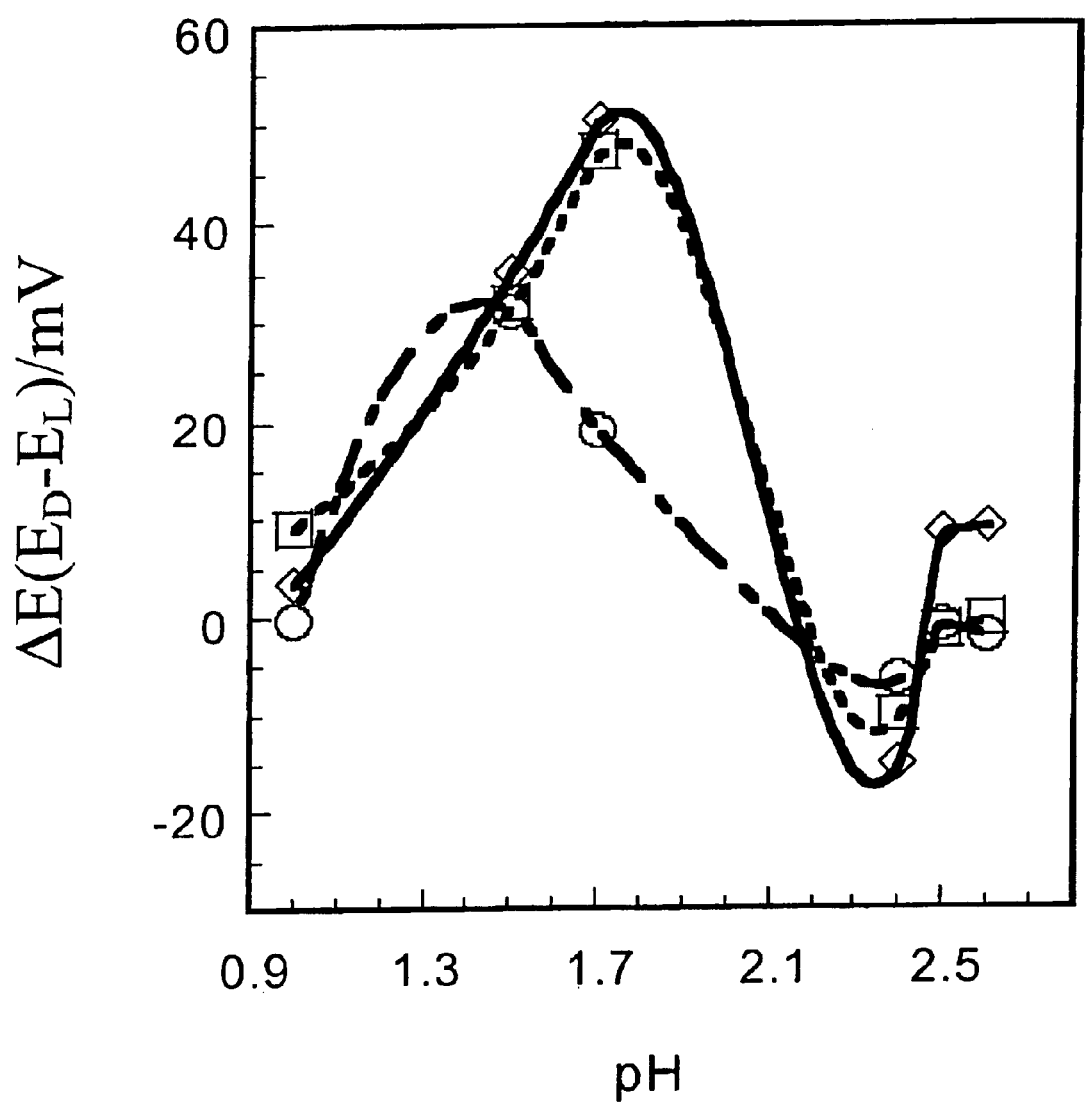
FIG. 5 is a graph that shows the effect of pH on the measured potential.

The difference in net charge of enantiomeric diastereoisomeric complexes enables them to be distinguished by potentiometry. As explained earlier, the enantiomers and chiral selector ligand are neutral at a certain pH, so they do not impact the potential measured by the potentiometric electrode. Thus, the predominant form of both aspartic acid and N-CBZ-L-Asp exist as zwitterions (neutral amino acids) at pH 2.3 ($pK_{a1}$=2.3[5] for N-CBZ-Asp and 2.1 for aspartic acid). As shown in FIGS. 3 and 5, the electrode demonstrated a negative potential response. Since the amino acids and the chiral selector ligand are neutral zwitterions in the reaction solution, the electrode's negative response is believed to be due to the anionic complexes in solution. The negative potential response, therefore, does not arise from the charge of the amino acids themselves, but from the net overall charge of the diastereoisomeric complexes. When the electrode was used to detect only Cu(II) ion, it gave a positive potential response, further supporting the above conclusion that a negative potential response is due to the charged diastereoisomeric complexes.

Figure 7:
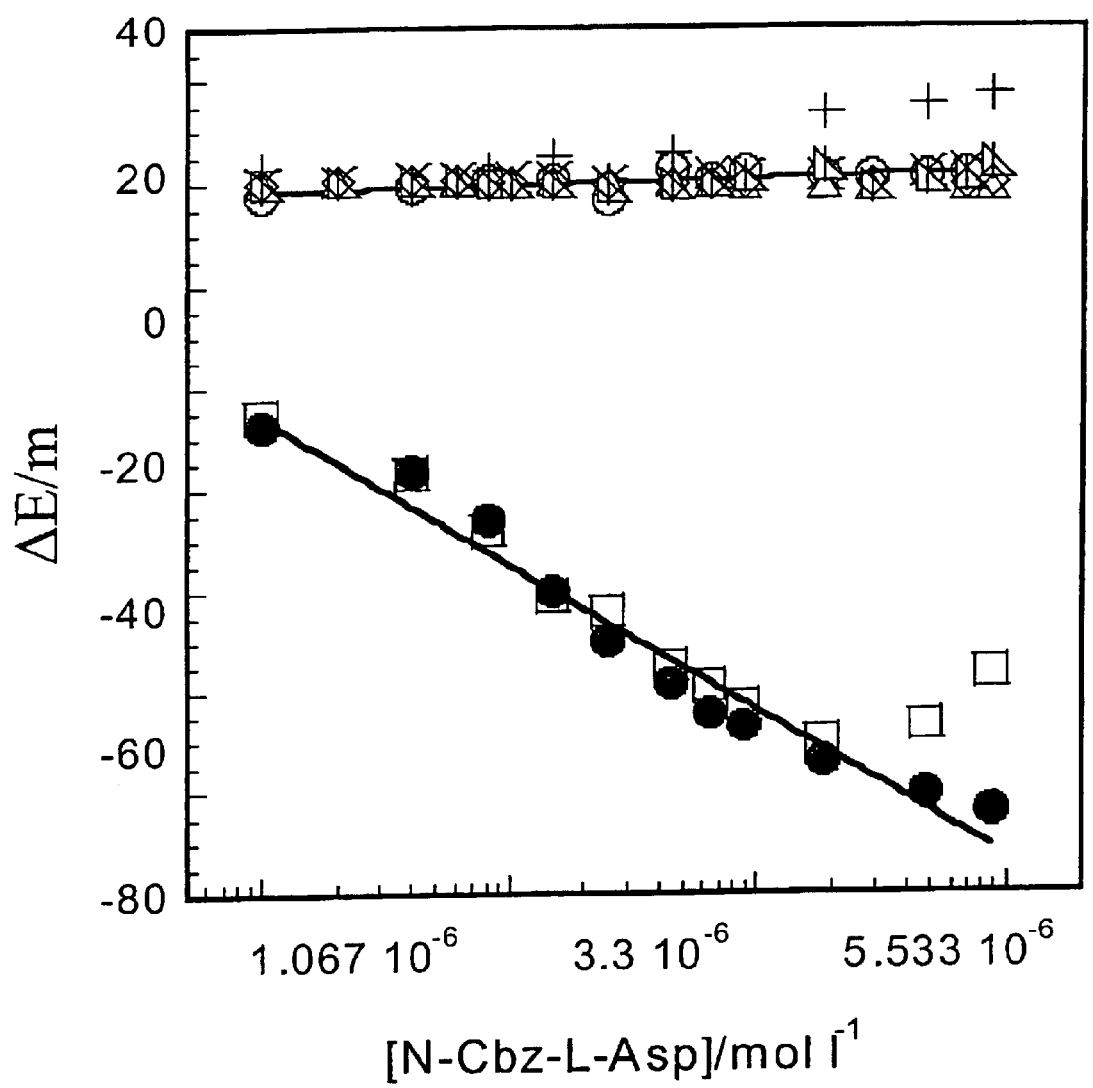
FIG. 7 is a graph that shows the chiral recognition for mixtures of enantiomers and chiral recognition for other amino acids.

Enantiomer concentration calibration curves are shown in FIG. 7. The potential response for the D-isomer is proportional to the logarithmic concentration with a slope of about $-29.2$ mV dec$^{-1}$ (n=2) in a concentration range of $1 \times 10^8 \sim 8.8 \times 10^6$ mol/L (FIG. 7, curve (○)). On the other hand, there is no change for L-isomer complex. The slope for the L-Asp was about 0 mV dec$^{-1}$ (FIG. 7, curve (○)). Furthermore, selective recognition of one enantiomer in the presence of the other is demonstrated (FIG. 7, curve (□, [D-Asp]/[L-Asp]=1000x; +, [L-Asp]/[D-Asp]=1000x)). The relative standard deviation was 1.2% for $1 \times 10^{-6}$ mol/L (n=11). The response time evaluated as the time required for a 95% signal response was about 3.5 min for $2.50 \times 10^{-7}$ mol/L D-Asp. Note that there is practically no response for other amino acids, for example, D-Phenylalanine (FIG. 7, curve(x)), D-Proline (Δ), D-Glutamate (□), D-Threonine (|), and D-D-Alalanine (◇), which demonstrates only ~0 mV potential difference (slopes of ~0 mV dec$^{-1}$). These results demonstrate the ability of the system to distinguish between enantiomers of the same amino acid as well as distinguish between different amino acids.

§4.4 Potentiometric Electrodes

Recall that the present invention distinguishes enantiomers by their different Nernst factors using potentiometry. As is known, potentiometry uses two electrodes: a reference electrode and an indicator (working) electrode. The potential of the reference electrode is constant and provides the reference potential against which analyte potential is measured. The indicator electrode measures the potential of the reaction of interest and varies with analyte concentration, among other things. The potential response of this electrode is defined as the difference between the electrode potential with and without the analyte, i.e. $\Delta E = E_1 - E_0$, where $E_0$ and $E_1$ are the electrode potentials before and after analyte addition, respectively.

The present invention can use both modified and unmodified indicator electrodes. A modified indicator electrode has the chiral selector ligand immobilized on its surface. Such a sensor can be fabricated via Polysiloxane Monolayer Immobilization (PMI). Briefly stated, PMI is a method for immobilizing a selector on a support surface by physical adsorption to a polysiloxane monolayer. Other immobilization techniques can be used instead. By combining chiral ligand exchange and potentiometry, the present invention can also recognize chiral compounds with unmodified electrodes. In another embodiment of the present invention, however, a modified electrode (referred to as a "chiral sensor" henceforth) is used to selectively identify an enantiomer.

A chiral sensor is an electrode modified with chiral selector ligand on its surface. When a chiral selector ligand forms a diastereoisomeric complex with the preferred enantiomer, the diastereoisomeric complex is immobilized on the surface of the chiral sensor. The net charge and the geometry of the diastereoisomeric complex, therefore, are important in enantiomeric recognition by chiral sensors.

One advantage of the present invention over certain previous methods for distinguishing enantiomers is that chiral ligand exchange potentiometry has an enantioselective detection system. The electrodes used in chiral ligand exchange potentiometry can translate an enantioselective molecular recognition event into a potential change that is recognizable by potentiometry, thereby allowing measurements to be taken without a previous separation step or a subsequent derivatization process.

§4.5 Exemplary Embodiments of the Potentiometric Electrodes

An exemplary embodiment of the general potentiometric electrode is described in §4.5.1. Then, an exemplary refinement of the potentiometric electrode, the chiral sensor, is described in §4.5.2.

§4.5.1 General Potentiometric Electrode

As previously described, potentiometry involves reference and indicator electrodes. In one embodiment of the present invention, a silver/silver chloride electrode is used as the reference electrode, and an ITO (indium-tin oxide) glass electrode is used as the indicator electrode. The surface sites on the electrode may be important in electrochemical enantiomeric discrimination. ITO is a degenerate n-type semiconducting material that has wide applications in optics and optoelectronics. Transmission electron microscopy results indicate that ITO has vertical columnar growth with multiple orientations. See, e.g., the article A. K. Kulkarni, et al., *Thin Solid Film*, 308–309: 1–7 (1997). The individual columns are single crystals and the grain sizes range from a few nanometers to a few tens of nanometers. The small sizes of these particles allow them to be physically close to the structures they recognize. Such particles therefore provide high resolution. See, e.g., the article C. R. Martin, et al., *Anal. Chem.*, 70: 322A (1998). Other indicator electrodes could be used to recognize chiral compounds including gold, silver and all other colloids modified electrodes, semiconductor oxide electrodes (such as $SnO_2$ electrodes), nanocrystalline $TiO_2$ film electrodes, etc. Other reference electrodes could also be used depending on the detection system, such as SCE, SSCE, Ag/AgCl, NHE, $Hg/HSO_4$, $Cu/CUSO_4$, etc.

§4.5.2 Exemplary Embodiment of the Chiral Sensor

Recently, methods combining monolayer molecular imprinting techniques with supporting electrolyte-free, buffer-free potentiometry were found to be effective in constructing chiral sensors. See, e.g., Y. Zhou, T. Nagoaka, *Chem. Sensor*, 14 (Suppl. B): 101 (1998); The present invention may create a molecular sensor by incorporating a chiral selector ligand onto the surface of a glass electrode. Such a modified electrode, or chiral sensor, can recognize isomers through forming diastereoisomeric complexes.

In one embodiment of the present invention, a molecular sensor is fabricated by Polysiloxane Monolayer Immobilization (PMI) using the chiral ligand selector N-CBZ-L-Asp as the selector molecule, which is comodified with octadecyltrichlorosilane (ODS) on the surface of an ITO glass electrode (ITO: 10 $\Omega cm^{-1}$). The ITO plate was soaked in a L- or D-CBZ-Asp suspension (6.7 g/L; solubility ~$10^{-6}$ M) of $CHCl_3/CCl_4$ (a volume ratio of 2:3) containing 0.8 mM ODS ($C_{18}H_{37}SiCl_3$) for three minutes to obtain a polysiloxane monolayer. The resulting chiral sensor was dried overnight at room temperature and then washed with water, completing the incorporation of the amino acid in the polysiloxane monolayer on the ITO surface, and rendering the modified electrode ready for use.

Basically, the molecular sensor may be fabricated by inserting the chiral selector (CBZ-Asp) into an organosiloxane monolayer. Such insertion may be accomplished by forming a hydrophobic layer of organosiloxane groups around the chiral selector molecules. The chiral selector molecule is dissolved in a low polarity medium on the impression, but it is present preferentially in aqueous solution. Elemental analysis results showed that carbon and silicon intensities of the modified electrode increased 88% and 32%, respectively, over the original electrode, indicating the chiral selector ligand was immobilized on the surface of the ITO glass electrode after performing PMI (See Table 1). For chiral ligand exchange potentiometry, the chiral selectors should typically be a chiral tridentate selector ligand capable of forming diastereoisomeric complexes with labile coordination complexes.

TABLE 1

| | Element analysis results | | | | | |
|---|---|---|---|---|---|---|
| | C | O | In* | Sn | N | Si |
| ITO glass plate | 186 | 189 | 100 | 6.6 | 7.9 | 7.65 |
| Adsorbed CBZ-Asp and ODS on ITO glass plate | 396.97 | 219.7 | 100 | 7.05 | 17.2 | 16.29 |

Figure 2:
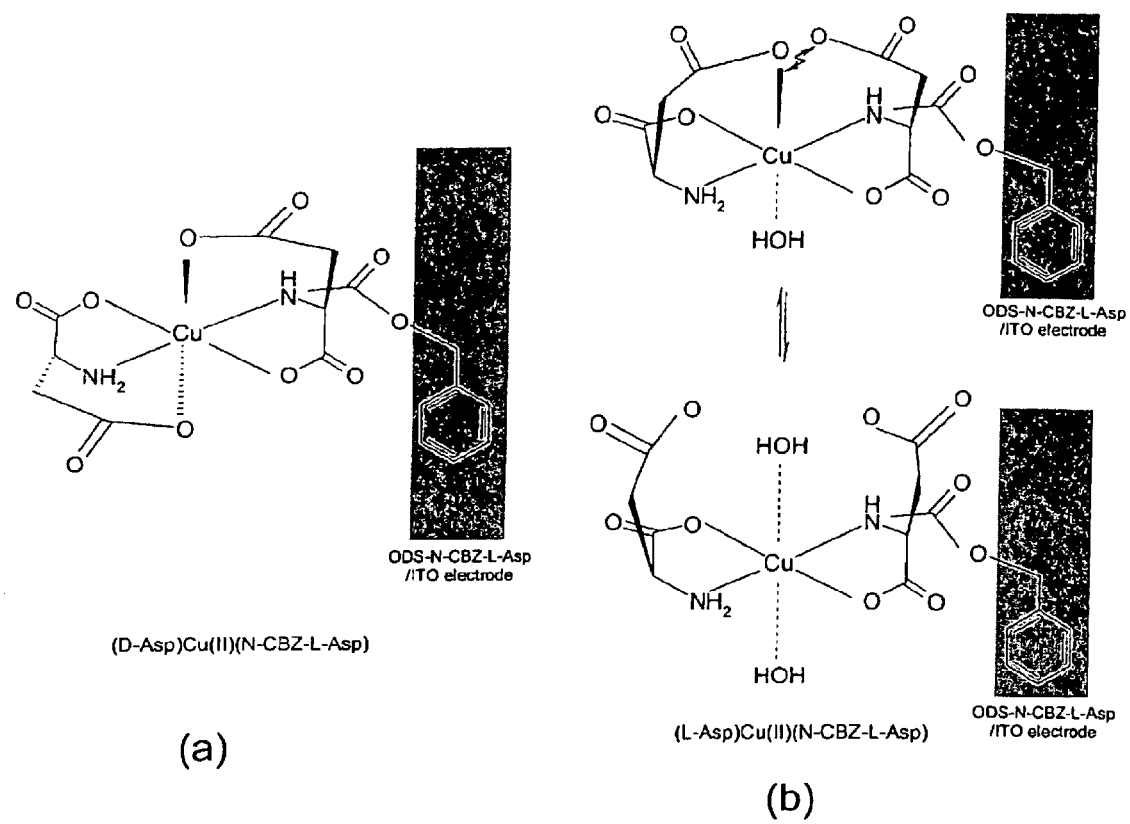
FIG. 2 depicts a second scheme having the structure of (a) the more stable complex (D-Asp)Cu(II)(N-CBZ-L-Asp), [DCuL], and (b) the less stable complex (L-Asp)Cu(II)(N-CBZ-L-Asp), [LCuL], on a modified D-aspartic acid sensor.

In the exemplary embodiment of the present invention, chiral CBZ-L-Asp is incorporated into the polysiloxane monolayer. This sensor, modified with L-amino acid derivative (N-CBZ-L-Asp) recognizes the D-aspartic acid in preference to the corresponding L-isomer, which forms diastereoisomeric complexes with amino acids and cupric ion added, and vice versa:

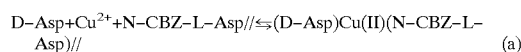
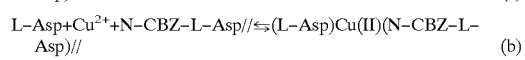

where CBZ-L-Asp// denotes optical CBZ-L-Asp immobilized on the surface of ITO electrode, as shown in FIG. 2.

Due to stereochemical influences, this modified electrode preferentially recognizes the D-isomer diastereoisomeric complex. Conversely, if N-CBZ-D-Asp is immobilized on the surface of the electrode, L-Asp could be recognized.

Figure 8:
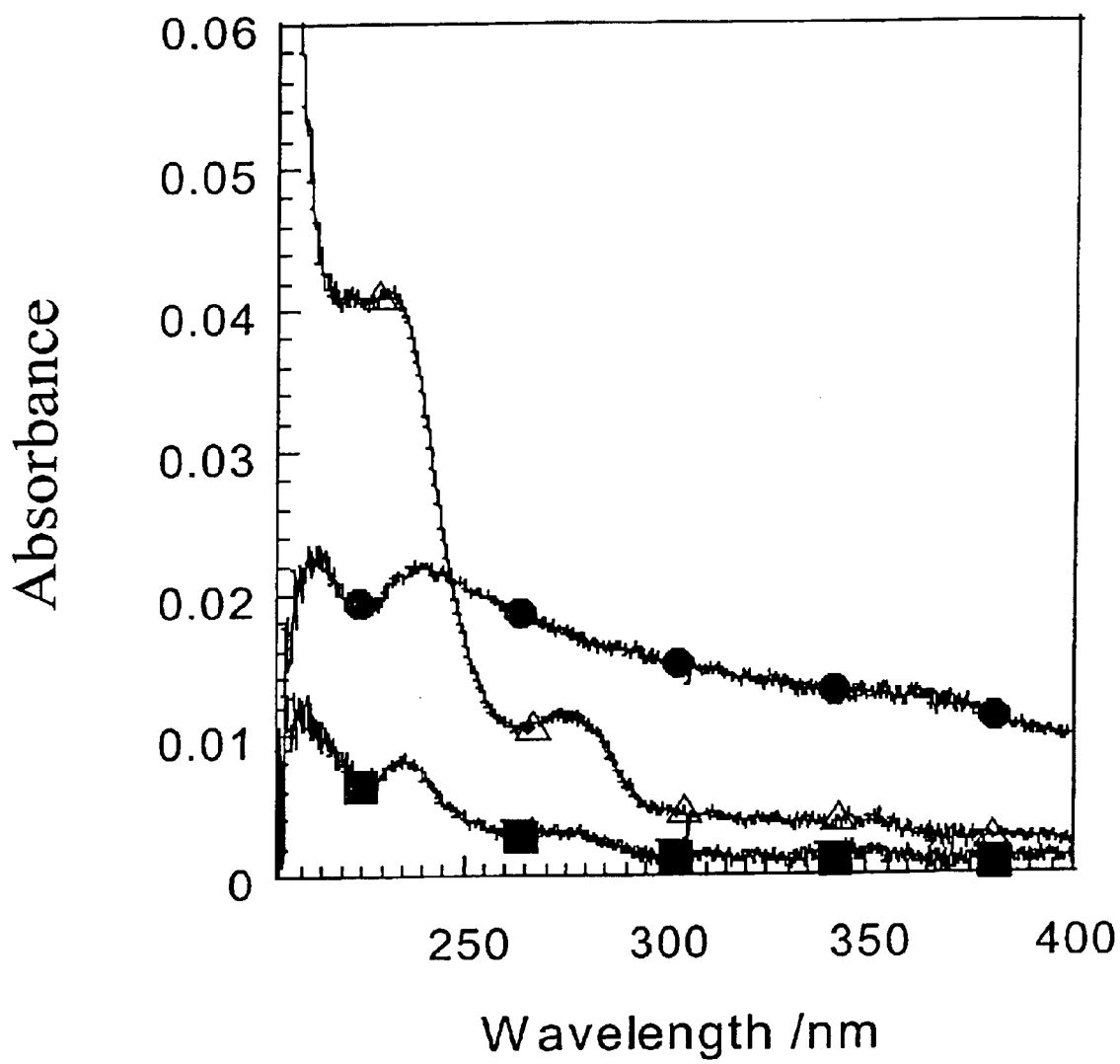
FIG. 8 is a graph that shows the ultraviolet-visible spectra of diastereoisomers formed by Order I and [Cu(N-CBZ-L-Asp)$_2$].

Chiral sensors distinguish enantiomers by means similar to unmodified electrodes except that the chiral selector ligand, and hence the diastereoisomeric complex, is immobilized on the surface of the modified electrode. As explained previously, the mechanism of enantiomeric discrimination in chiral ligand exchange potentiometry, whether modified or unmodified electrodes are used, is based on stereochemical influences in complex formation and the resulting net charge of the diastereoisomeric complex. In FIG. 8, curve (○), the UV-Vis intensity of peaks (232 nm) of it was increased due to the stronger complexion compared to [Cu(N-CBZ-L-Asp)$_2$] and a new peak appeared at 278 nm. For the equally paired L-Cu-L complex (▽), both two β-carboxyl groups were in the same part of the planar, as shown in FIG. 2(b). The crowded space would influence the complexion. Such a complex should be sterically prohibited. In addition, its UV-Vis peak intensity (FIG. 8 (■)) decreased compared to [(D-Asp)Cu(II)(N-CBZ-L-Asp)] and [Cu(II)(N-CBZ-L-Asp)$_2$] (as shown in FIG. 10 curve (Δ) and (○)).

Figure 9:
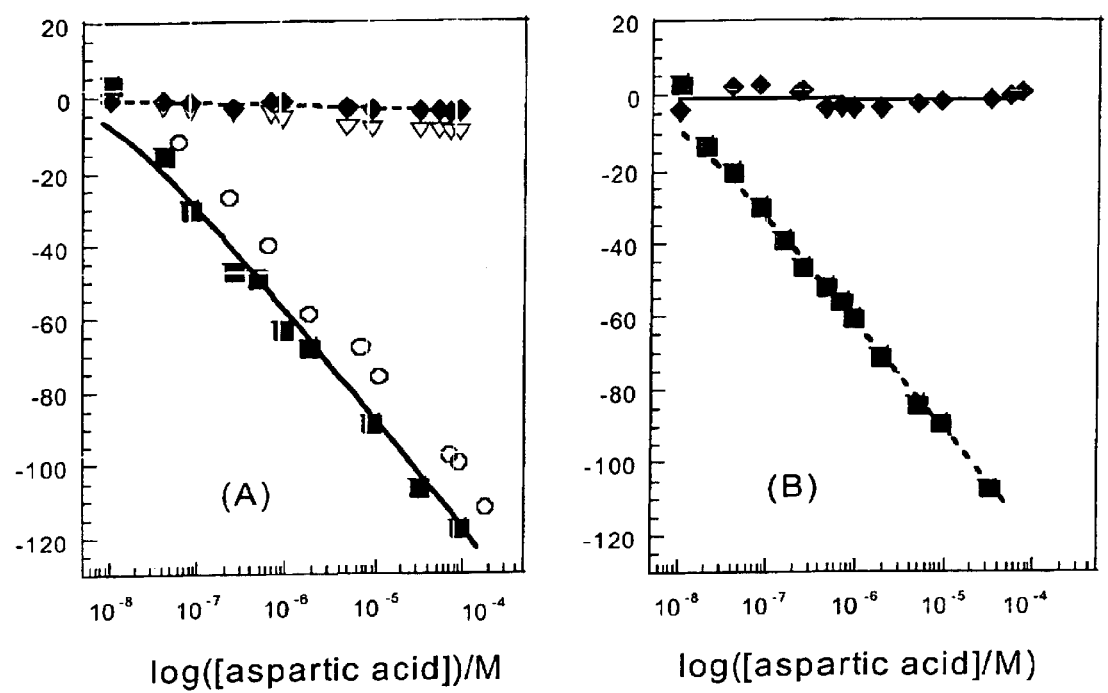
FIG. 9 is a graph that shows the chiralselective potential responses of (A) D- and (B) L-aspartic acid sensors for D-aspartic acid and L-aspartic acid.

The chiral discrimination toward binding of enantiomers of the labile coordination complex [Cu(D-Asp)$_2$] was investigated, and chiral molecular sensors were shown to have preference for a particular isomer. The D-aspartic acid sensor (chiral selector: N-CBZ-L-Asp) was found to correctly identify the D-aspartic acid isomer (■). The potential response was proportional to the logarithmic concentration in a concentration range of $4.00 \times 10^{-8}$–$8.9 \times 10^{-5}$ M, while there was no change for the L-isomer complex (♦) (FIG. 9, (see FIG. 9, curve (○, [Asp]=0; ▽, [L-Asp]=$1 \times 10^{-6}$)), but also demonstrated very specific molecular recognition ability. The sensor could only have high response towards one enantiomeric complex in a mixture of D- and L-isomers, as shown in Table 2:

TABLE 2

Outputs of sensors for racemic samples (50% L-Asp and 50% D-Asp)

| | D-Asp sensor output/mV | | |
|---|---|---|---|
| Concentration/mM * | 50% D- and 50% L-isomers | 100% D-isomer | Error % |
| $1.00 \times 10^{-7}$ | −29.57 | −30.25 | −2.25 |
| $6.25 \times 10^{-7}$ | −53.75 | −54.51 | −1.40 |
| $1.30 \times 10^{-6}$ | −63.97 | −64.2 | −0.36 |
| $5.00 \times 10^{-6}$ | −83.27 | −82.04 | 1.50 |
| $8.50 \times 10^{-6}$ | −89.75 | −89.06 | 0.78 |
| $4.98 \times 10^{-5}$ | −106.58 | −112.47 | −5.24 |
| $6.95 \times 10^{-5}$ | −114.79 | −116.88 | −1.79 |

* Concentrations of L- and/or D-Asp

The results predict potential decreases of 3.56% in the presence of the equimolar amounts of the L-aspartic acid. The fact that no substantial potential difference was observed with and without L-isomer demonstrates high selectivity ability as shown from the selectivity coefficients.

Selectivity coefficients were determined by the separate solution method and $K_{Dj}^{POT}$ (D: D-aspartic acid, j: interfering amino acids) values obtained are shown in Table 3, below:

TABLE 3

Selectivity coefficients of other amino acids against D-Asp

| Amino acids | D-Glu | D-Pro | D-Phe | D-His | D-Ala | D-Thr | D-Val |
|---|---|---|---|---|---|---|---|
| $K_{Dj}^{POT}$ | $1.1 \times 10^{-4}$ | $1.5 \times 10^{-3}$ | $5.4 \times 10^{-3}$ | $1.1 \times 10^{-3}$ | $5.4 \times 10^{-3}$ | $4.8 \times 10^{-3}$ | $1.1 \times 10^{-3}$ | curve (■,♦)). Selectivity coefficients, $K_{DL}^{POT}$, were established by separate solution method and mixed solution method. See, e.g., K. Umezawa, Y. Umezawa, *Handbook of Ion-Selective Electrodes*, 3 (1998) (This text is incorporated herein by reference.):

$$E_D = E_D^0 + s \log(1 + K_D[D\text{-}Asp] + K_L[L\text{-}Asp]) \quad (1)$$

$$K_{DL}^{POT} = \frac{K_L}{K_D} \quad (2)$$

where $E_D$ is the potential of the sensor and $E_D^0$ is the standard electrode potential, s (−29.6 mV/dec) is the slope, and $K_{DL}^{POT}$ is the selectivity coefficient. By simulation (with targeted isomer concentrations of zero (O)), $K_{DL}^{POT}$ (A) values of $4.0 \times 10^{-5}$ (separate solution method) and $5.0 \times 10^{-5}$ (mixed solution method) have been obtained for the D-aspartic acid sensor and $K_{LD}^{POT}$ (B) values of $5.0 \times 10^{-5}$ (separate solution method) for L-aspartic acid sensor. Furthermore, this sensor not only demonstrated selective recognition of one enantiomer in the presence of the other The high preference for D-aspartic acid is evident. There was practically no response for other amino acids, even those structurally similar to aspartic acid, such as D-glutamic acid. Chiral sensors therefore demonstrate the ability to discriminate between amino acids and between enantiomers of an amino acid.

The response time evaluated as the time required for a 95% signal response was about 220 s for $8 \times 10^{-7}$ M D-aspartic acid. After repeating the measurement more than 200 times, the potential response only decreased to 92% of its initial magnitude. The relative standard deviation was 1.67% for $3.0 \times 10^{-7}$ M (n=16).

While this invention has been described with an emphasis upon an exemplary embodiment, it will be apparent to those of ordinary skill in the art that variations of the exemplary embodiment may be used and that it is intended that the invention may be practiced otherwise than as specifically described herein. Accordingly, this invention includes all modifications encompassed within the spirit and scope of the invention as defined by the following claims.

What is claimed is:

1. A method for detecting a particular enantiomer of an enantiomer pair, the method comprising:
   a) providing a solution including one, or both enantiomers of the enantiomer pair, a metal ion, and a chiral selector ligand;
   b) measuring, by potentiometry, the potential of the solution; and
   c) determining whether or not the solution includes the particular enantiomer of the enantiomer pair based on the potential.

2. The method of claim 1 wherein the potential of the solution is measured using an electrochemical detection system including a potentiometeric electrode, a reference electrode, a magnetic stirrer, a magnetic bar and a electrometer.

3. The method of claim 1 wherein the solution includes both enantiomers of the enantiomer pair.

4. The method of claim 1 wherein the solution of zero, one, or both enantiomers, metal ion, and chiral selector ligand is provided by first combining the zero, one, or both enantiomers and the metal ion, and then later adding the chiral selector ligand.

5. The method of claim 1 wherein the particular enantiomer of the enantiomer pair is a tridentate enantiomer.

6. The method of claim 5 wherein the tridentate enantiomer is selected from a group consisting of amino acids, amino acid derivatives, and chiral drugs.

7. The method of claim 1 wherein the particular enantiomer of the enantiomer pair is selected from a group consisting of amino acids, amino acid derivatives, and chiral drugs.

8. The method of claim 1 wherein the particular enantiomer of the enantiomer pair can displace a water molecule at the axial position of a labile coordination complex formed by the enantiomer and metal ion.

9. The method of claim 1 wherein the chiral selector ligand and the particular enantiomer of the enantiomer pair are of comparable sizes and shapes.

10. The method of claim 1 wherein the solution includes one or both enantiomers of the enantiomer pair, and
    wherein a labile coordination complex is formed by at least one of the one or both enantiomers and the metal ion in the solution.

11. The method of claim 10 wherein the chiral selector ligand undergoes ligand exchange with the labile coordination complex to form a diastereoisomeric complex.

12. The method of claim 11 wherein the one or both enantiomers' diastereoisomeric complexes have different spatial structure and different net charges.

13. The method of claim 11 wherein the potential of the solution is based on net charges of the diastereoisomeric complexes.

14. A method for detecting a particular enantiomer of an enantiomer pair, the method comprising:
    a) providing a solution including zero, one, or both enantiomers of the enantiomer pair and a metal ion;
    b) measuring, by potentiometry, the potential of the solution using an electrode modified with a chiral selector ligand; and
    c) determining whether or not the particular enantiomer of the enantiomer pair exists based on the potential measured, wherein the particular enantiomer of the enantiomer pair is a tridentate amino acid or another tridentate enantiomer.

15. The method of claim 14 wherein the tridentate enantiomer is selected from a group consisting of amino acids, amino acid derivatives, and chiral drugs.

16. A method for detecting a particular enantiomer of an enantiomer pair, the method comprising:
    a) providing a solution including one or both enantiomers of the enantiomer pair and a metal ion;
    b) measuring, by potentiometry, the potential of the solution using an electrode modified with a chiral selector ligand; and
    c) determining whether or not the particular enantiomer of the enantiomer pair exists based on the potential measured, wherein the particular enantiomer of the enantiomer pair can displace a water molecule at the axial position of a labile coordination complex formed by the one or both enantiomers and metal ion.

17. A method for detecting a particular enantiomer of an enantiomer pair, the method comprising:
    a) providing a solution including zero, one, or both enantiomers of the enantiomer pair and a metal ion;
    b) measuring, by potentiometry, the potential of the solution using an electrode modified with a chiral selector ligand; and
    c) determining whether or not the particular enantiomer of the enantiomer pair exists based on the potential measured, wherein the chiral selector ligand and the zero, one, or both enantiomers are of comparable sizes and shapes.

18. A method for detecting a particular enantiomer of an enantiomer pair, the method comprising:
    a) providing a solution including zero, one, or both enantiomers of the enantiomer pair and a metal ion;
    b) measuring, by potentiometry, the potential of the solution using an electrode modified with a chiral selector ligand; and
    c) determining whether or not the particular enantiomer of the enantiomer pair exists based on the potential measured, wherein the solution includes one or both enantiomers of the enantiomer pair, and
    wherein a labile coordination complex is formed by at least one of the one or both enantiomers and the metal ions in the solution.

19. The method of claim 18 wherein the chiral selector ligand is incorporated onto the surface of the electrode and the chiral selector ligand undergoes ligand exchange with the labile coordination complex to form a diastereoisomeric complex that is immobilized on the surface of the electrode.

20. The method of claim 19 wherein the one or both enantiomers' diastereoisomeric complexes have different spatial structures and different net charges.

21. The method of claim 20 wherein the measured potential of the solution corresponds to net charges of the diastereoisomeric complexes.

* * * * *